United States Patent
Masumoto et al.

(10) Patent No.: US 9,036,882 B2
(45) Date of Patent: May 19, 2015

(54) DIAGNOSIS ASSISTING APPARATUS, DIAGNOSIS ASSISTING METHOD, AND RECORDING MEDIUM HAVING A DIAGNOSIS ASSISTING PROGRAM STORED THEREIN

(75) Inventors: Jun Masumoto, Minato-ku (JP); Masaki Miyamoto, Minato-ku (JP)

(73) Assignee: FUJIFILM Corporation, Tokyo (JP)

( * ) Notice: Subject to any disclaimer, the term of this patent is extended or adjusted under 35 U.S.C. 154(b) by 716 days.

(21) Appl. No.: 13/264,863

(22) PCT Filed: Apr. 15, 2010

(86) PCT No.: PCT/JP2010/002749
§ 371 (c)(1),
(2), (4) Date: Oct. 17, 2011

(87) PCT Pub. No.: WO2010/119690
PCT Pub. Date: Oct. 21, 2010

(65) Prior Publication Data
US 2012/0033866 A1    Feb. 9, 2012

(30) Foreign Application Priority Data

Apr. 16, 2009   (JP) ................................. 2009-100383
Mar. 30, 2010   (JP) ................................. 2010-078622

(51) Int. Cl.
*G06T 7/00*    (2006.01)
*G06T 3/00*    (2006.01)
(Continued)

(52) U.S. Cl.
CPC ................. *G06T 19/00* (2013.01); *A61B 5/055* (2013.01); *A61B 5/4255* (2013.01); *A61B 6/466* (2013.01)

(58) Field of Classification Search
CPC ... G06T 11/003; G06T 7/0012; G06T 7/0024; G06T 7/0028; G06T 3/0025; G06T 3/0031; G06T 3/0037; G06T 3/0043; A61B 5/00; A61B 5/0033; A61B 5/0037; A61B 5/742; A61B 5/7425; A61B 6/463; A61B 6/5223; A61B 2019/5289
USPC .......... 382/131, 128, 132; 600/425, 426, 101, 600/103
See application file for complete search history.

(56) References Cited

U.S. PATENT DOCUMENTS 6,369,812 B1 *   4/2002   Iyriboz et al. ................. 345/419
8,254,653 B2 *   8/2012   Scheuering et al. .......... 382/131
(Continued)

FOREIGN PATENT DOCUMENTS

JP    2006-068301 A    3/2006
JP    2008-259712 A    10/2008
(Continued)

OTHER PUBLICATIONS

Wegenkittl, et al. "Mastering Interactive Virtual Bronchioscopy on a Low-end PC." VIS '00 Proceedings of the conference on Visualization. (2000): 461-464. Print.*

(Continued)

*Primary Examiner* — Michael A Newman
(74) *Attorney, Agent, or Firm* — Sughrue Mion, PLLC (57) ABSTRACT

Overview images that represent the overview of a structure (e.g., the large intestine) are generated based on volume data, and displayed on a screen. Points within the overview images and points corresponding thereto in the volume data are set as target points. A target volume that includes the target points and line of sight vectors within the volume data having the target points as endpoints and a movable viewpoint as a starting point are set within the volume data. The directions of the line of sight vectors are changed by moving the viewpoint, and the target volumes are projected onto projection planes perpendicular to the directions of the line of sight vectors to generate detailed images that represent details of the structure in the vicinity of the target points. The detailed images are displayed on the screen.

15 Claims, 8 Drawing Sheets

(51) Int. Cl.
    *A61B 5/00*    (2006.01)
    *A61B 19/00*   (2006.01)
    *A61B 5/055*   (2006.01)
    *A61B 6/00*    (2006.01)
    *G06T 19/00*   (2011.01)

(56) References Cited

U.S. PATENT DOCUMENTS

| | | | |
|---|---|---|---|
| 8,538,113 B2 * | 9/2013 | Tanaka et al. | 382/131 |
| 2004/0233222 A1 * | 11/2004 | Lee et al. | 345/621 |
| 2006/0221074 A1 | 10/2006 | Matsumoto | |
| 2008/0175461 A1 * | 7/2008 | Hentschel | 382/131 |
| 2009/0002366 A1 * | 1/2009 | Kanitsar et al. | 345/419 |
| 2010/0215226 A1 * | 8/2010 | Kaufman et al. | 382/128 |

FOREIGN PATENT DOCUMENTS

| | | |
|---|---|---|
| JP | 2008-259713 A | 10/2008 |
| WO | 2009/016927 A1 | 2/2009 |

OTHER PUBLICATIONS

Hauser, et al. "Two-level volume rendering—fusing MIP and DVR." IEEE Proceedings Visualization. (2000): 211-218. Print.*

Neugebauer, et al. "Combining Map Displays and 3D Visualizations for the Analysis of Scalar Data on Cerebral Aneurysm Surfaces." Eurographics/IEEE-VGTC Symposium on Visualization. 28.3 (2009): 1-8. Print.*

Wegenkittl et al. "Mastering Interactive Virtual Bronchioscopy on a Low-end PC." VIS '00 Proceedings of the conference on Visualization. (2000): 461-464. Print.*

Seitz, Image-Based Transformation of Viewpoint and Scene Appearance. Diss. University of Wisconsin, 1997. Print.*

Hauser et al. "Two-level volume rendering—fusing MIP and DVR." IEEE Proceedings Visualization. (2000): 211-218. Print.*

Halle, Michael. Multiple Viewpoint Rendering for Three-Dimensional Displays. Thesis. Massachusetts Institute of Technology, 1997. Print.*

Gortler, et al. Creating and Rendering Image-Based Visual Hulls. Tech. Rep. Massachusetts Institute of Technology, 1999. Print.*

* cited by examiner

DIAGNOSIS ASSISTING APPARATUS, DIAGNOSIS ASSISTING METHOD, AND RECORDING MEDIUM HAVING A DIAGNOSIS ASSISTING PROGRAM STORED THEREIN

CROSS REFERENCE TO RELATED APPLICATIONS

This application is a National Stage of International Application No. PCT/JP2010/002749, filed on Apr. 15, 2010, which claims priority from Japanese Patent Application Nos. 2009-100383, filed on Apr. 16, 2009, and 2010-078622filed Mar. 30, 2010, the contents of all of which are incorporated herein by reference in their entirety.

TECHNICAL FIELD

The present invention is suited for utilization in the medical field, and is related to a system and a method for assisting image diagnosis using three dimensional image data. The present invention is also related to a computer readable recording medium having a diagnosis assisting computer program stored thereon.

BACKGROUND ART

Apparatuses that convert three dimensional image data (volume data) such as 3DCT (Three Dimensional Computed Tomography) images into images suited for observation and display these images have been proposed as apparatuses for assisting image diagnosis by radiologists. Known conversion methods include: VR (Volume Rendering); MIP (Maximum Intensity Projection); and MPR (Multi Planar Reconstruction).

Images suited for observation differ according to observation targets and the purposes of observation. VE (Virtual Endoscopy) images are suited for observation of the inner walls of hollow tubular organs. In addition, images that represent tubular hollow organs which are linearly extended then cut open along the cores thereof (extension expanded images) and images that represent tubular hollow organs which are linearly extended then cut into cross sections perpendicular to the cores thereof (extension sectional images) are preferred, as they enable the entireties of tubular hollow organs to be observed in short amounts of time (refer to Patent Document 1).

However, virtual Endoscopy images, extension expanded images, and extension sectional images are images that capture images of the inner walls of tubular hollow organs from a single direction, and therefore there are many portions that do not appear in such images. For example, there are a great number of folds in the inner wall of the large intestine. However, if the direction of a line of sight which is set when an image is generated is perpendicular to the side wall of a fold, diseased portions (polyps, for example) which are present on the rear surface or behind the fold will not appear in the generated image. In addition, there are cases in which diagnosis is difficult even if diseased portions appear in images, if observation is only from a single direction. For example, fine recesses and protrusions of inner walls are difficult to discern by observation from directions perpendicular thereto, and there are cases in which polyps and recesses, and folds and grooves cannot be distinguished.

As a solution to this problem, Patent Document 2 (particularly, paragraph 0039) proposes a method in which the direction of a virtual light beam emitted from a virtual viewpoint is variable, and projection images from different images are displayed either alongside each other or as an animated series of images. In addition, Patent Document 3 proposes a method in which a display range movable in the direction of the core of a tubular hollow organ (the extension direction in an extension image), lines of sight are set such that they are perpendicular to an inner wall at regions corresponding to the center of the display range, and become smaller acute angles at regions further away from the center of the display range, and images that represent each of the regions are generated. In this method, the directions of set lines of sight will differ for the same location along the inner wall if the location is displayed as the center of the display range and displayed as the ends of the display range. Thereby, structures can be observed from different angles by changing the display range.

PRIOR ART DOCUMENTS

[Patent Document 1]
 Japanese Unexamined Patent Publication No. 2008-259712
[Patent Document 2]
 Japanese Unexamined Patent Publication No. 2006-068301
[Patent Document 3]
 Japanese Unexamined Patent Publication No. 2008-259713

There are regions that cannot be sufficiently observed in complex structures such as the inner walls of large intestines, even if the directions of lines of sight are changed. For example, in the case that a polyp and a fold are in close proximity to each other, it may not be possible to sufficiently observe the polyp if the fold blocks the set lines of sight when it is desired to observe the polyp from the side of the fold.

In addition, extension expanded images and extension sectional images represent tubular hollow organs which are virtually deformed. Therefore, there are cases in which the shapes and sizes of diseased portions that appear in these images differ from the actual shapes and sizes thereof. For example, a polyp which is present on an inner wall of the large intestine at a bent portion thereof is virtually extended along with the extension of the bent portion. Therefore, the shape and size of the polyp that appears in an extension expanded image or an extension sectional image will differ from the actual shape and size thereof.

The object of the present invention is to provide an improved diagnosis assisting apparatus, an improved diagnosis assisting program, and an improved diagnosis assisting method such that a physician who performs diagnosis can sufficiently observe locations which are considered to be diseased portions and locations at which diseased portions are likely to be hidden from various directions, and also can obtain accurate information regarding the shapes and the sizes of such locations by observation.

DISCLOSURE OF THE INVENTION

A diagnosis assisting apparatus of the present invention is equipped with a volume data storing means, an overview image display means, a target point setting means, a target volume setting means, a line of sight setting means, and a detailed image display means, to be described below. In addition, a diagnosis assisting program of the present invention is installed on one or a plurality of computers, and when executed, causes the one or the plurality of computers to function as the volume data storing means, the overview image display means, the target point setting means, the target volume setting means, the line of sight setting means, and the detailed image display means. The diagnosis assisting program of the present invention is constituted by a plurality of program modules. The functions of each of the aforementioned means are realized by one or a plurality of program modules. The group of program modules is provided to users by being recorded in storage media such as CD-ROM's and DVD's, by being recorded in a storage unit attached to a server computer in a downloadable state, or by being recorded in network storage in a downloadable state. A diagnosis assisting method of the present invention is a method that assists diagnosis, by causing one or a plurality of computers to execute the processes of the volume data storing means, the overview image display means, the target point setting means, the target volume setting means, the line of sight setting means, and the detailed image display means.

The volume data storing means stores a plurality of sets of volume data, constituted by data obtained by imaging subjects. Specifically, an internal memory or a storage of a computer that functions as the diagnosis assisting apparatus, an external storage device which is connected to the computer either directly or via a network, or the like, function as the volume data storing means.

The volume data storing means stores therein sets of volume data obtained by other computers reconstructing data (slice data, etc.) output from imaging apparatuses, in addition to sets of volume data output from imaging apparatuses. In addition, the volume data storing means is also capable of storing sets of volume data which have been processed by functions of the diagnosis assisting apparatus (for example, sets of volume data from which data regarding specific structures such as bones have been deleted) after subjects are imaged.

The overview image display means generates overview images of structures that constitute the subjects based on the volume data, and displays the overview images on a screen. The overview images are one or a plurality of images for aiding understanding of the entirety of the structure. Preferably, the overview images are single images that represent the entirety of the structure. However, the overview images may be a plurality of images that represent sections of the structure, which is divided into a plurality of sections. The overview images may be VR images. In the case that the structure is a tubular structure, it is preferable for the overview images to be the aforementioned extension expanded image, the extension sectional image, or a virtual endoscopy image.

The target point setting means sets at least one point within the overview images and at least one point within the volume data corresponding to the at least one point within the overview images as target points. The target points are points of interest, that is, points at which careful observation is required to perform diagnosis. The target points are set manually or automatically.

In the case that the target points are set manually, the target point setting means detects user operations that specify points within the overview images displayed on the screen, and sets the point specified by the user operations and the points within the volume data corresponding to the points as the target points. The method described in Patent Document 1 or any other known method may be employed to search for the points within the volume data corresponding to the points within the overview images. In the case that the target points are manually set, users can specify desired points as the target points, and locations at which detailed observation is desired can be observed as desired.

In the case that the target points are set automatically, the target point setting means detects characteristic portions of the structure by analyzing the volume data, and sets points within the overview images that indicate the positions of the characteristic portions and points within the volume data that indicate the positions of the characteristic portions as the target points. Various automatic detection methods which are employed by known CAD (Computer Aided Diagnosis) systems may be employed to detect the characteristic portions. In the case that the target points are set automatically, points that require careful observation will be set without any omissions and without placing a burden on users.

The target volume setting means sets a target volume that includes the target points within the volume data. The target volume is a section of the volume data, and is constituted by a voxel data group positioned around the peripheries of the target points from among voxel data that constitutes the volume data.

The target volume setting means refers to data regarding the shape and the size of a target volume which is stored in a predetermined recording medium, and sets a target volume having a shape and a size indicated by the data. Alternatively, the target volume setting means detects characteristic portions of the structure by analyzing the volume data, and sets a target volume having a shape and a size which are determined based on the shapes and the sizes of the characteristic portions. In the former setting method, the shape and size of the target volume may be set in advance, to reduce processing time. In the latter setting method, a target volume having an optimal shape and an optimal size can be set for each detected characteristic portion.

The line of sight setting means sets line of sight vectors within the volume data having the target points as endpoints and a movable viewpoint as a starting point, and changes the directions of the line of sight vectors by moving the viewpoints. The movement of the viewpoint may be performed automatically. However, it is preferable for the line of sight setting means to detect user operations that command movement of the viewpoint, and to move the viewpoint based on the user operations. In this case, users may observe images as desired without being restricted by time.

The detailed image display means projects the target volumes onto projection planes perpendicular to the directions of the line of sight vectors to generate detailed images that represent details of the structure in the vicinity of the target points, and displays the detailed images on the screen. As described previously, the directions of the line of sight vectors are changed accordingly to settings. Therefore, the detailed image display means generates and displays new detailed images each time that the directions of the line of sight vectors are changed. When new detailed images are generated and displayed, the orientation of the detailed images within the screen change. Thereby, users are enabled to observe structures in the vicinities of the target points from various directions.

The detailed images may be displayed alongside the overview images. However, it is preferable for the detailed images to be displayed such that they overlap positions within the overview images at which the target points are set. If the positions of the target points and the display positions of the detailed images are the same, the series of operations of specifying the target points and moving the viewpoint can be performed without moving the mouse over a great distance.

The detailed images are displayed on the screen as though portions of the overview images are enlarged. However, the detailed images are not generated based on the overview images, but generated by projecting the target volume onto a projection plane by transparent projection (central projection) or parallel projection. Accordingly, the detailed images are those that represent the structures in the vicinities of the target points with greater accuracy than the overview images. Meanwhile, the target volume which is employed to generate the detailed images does not include any data related to structures outside the set range thereof. Therefore, structures outside the range of the target volume do not appear in the detailed images.

The detailed image display means may generate a plurality of projected images of the target volume by a plurality of projection methods, and combine the plurality of projected images to generate the detailed images. By adopting this configuration, the detailed images will be those that include various types of information obtained from each type of projected image. By displaying such detailed images, more diagnostic information can be provided to users compared to a case in which a single projected image is displayed as the detailed image.

The overview image display means may generate and display a plurality of overview images for each of a plurality of body positions, based on sets of volume data related to a plurality of body positions obtained by performing imaging with different body positions; and the detailed image display means may generate and display a plurality of detailed images employing target volumes which are set in each of the plurality of sets of volume data for each of the plurality of body positions. Diagnostic accuracy can be employed by enabling observations of images obtained by imaging with different body positions.

According to the diagnosis assisting apparatus, the diagnosis assisting program, and the diagnosis assisting method of the present invention, users are enabled to visually understand the entirety of a structure, and then can observe the vicinities of the target points of the structure in detail. The users can observe the structure in the vicinities of the target points from various angles, because the directions of the lines of sight can be changed during observation of the detailed images. At this time, structures outside of the range of the target volume do not appear in the detailed images. Therefore, even if the directions of the lines of sight are changed, the structure in the vicinities of the target points will not be hidden behind other structures. In addition, the detailed images represent the structure (the shape and the size thereof) more accurately than the overview images. Accordingly, the users can obtain more accurate information regarding the structure by observing the detailed images.

BEST MODE FOR CARRYING OUT THE INVENTION

Hereinafter, embodiments of the diagnosis assisting apparatus and the diagnosis assisting program of the present invention will be described in detail with reference to the attached drawings.

In the embodiments to be described below, the diagnosis assisting apparatus is a computer, in which a diagnosis assisting program according to each embodiment is installed. The computer may be a work station or a personal computer which is directly operated by a physician who performs diagnoses. Alternatively, the computer may be a server computer which is connected to such a work station or personal computer via a network. The diagnosis assisting programs are distributed by being recorded in storage media such as CD-ROM's and DVD's, and installed in the computer from the storage media. Alternatively, the diagnosis assisting program is recorded in a storage unit attached to a server computer in a state in which it is accessible from the exterior, or recorded in network storage in a state in which it is accessible from the exterior, and downloaded to and installed in computer utilized by the physician as necessary.

Figure 1:
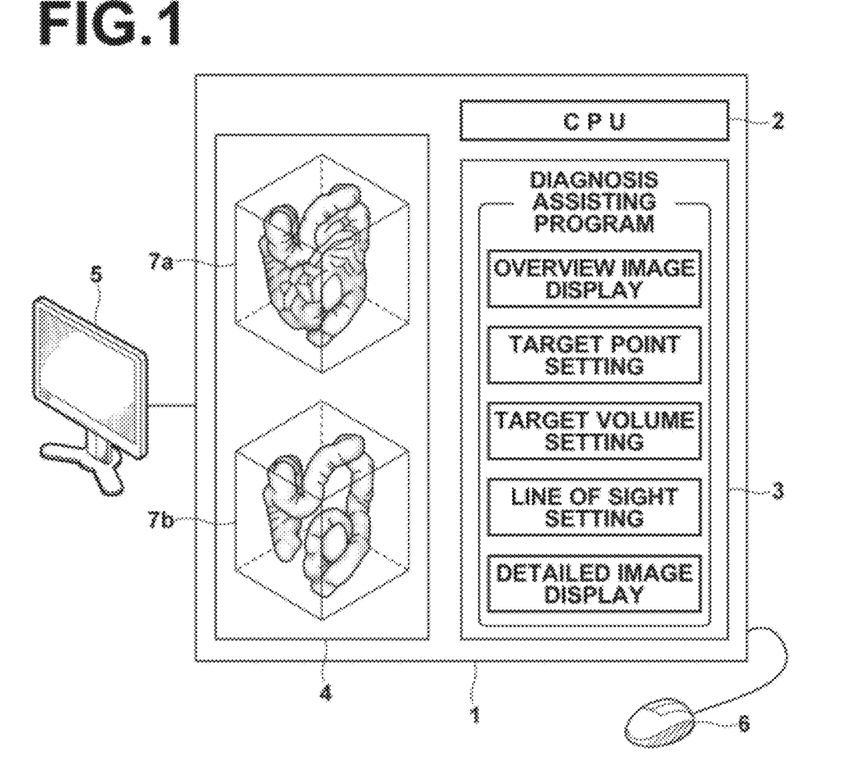
FIG. 1 is a diagram that illustrates the schematic structure of a diagnosis assisting apparatus according to an embodiment of the present invention.

FIG. 1 is a diagram that illustrates the schematic structure of a diagnosis assisting apparatus 1, which is realized by installing a diagnosis assisting program into a work station. As illustrated in FIG. 1, the diagnosis assisting apparatus 1 is equipped with a CPU 2, a memory 3, and a storage 4, as is standard for a work station. In addition, a display 5 and input devices, such as a mouse 6, are connected to the diagnosis assisting apparatus 1.

Volume data, which are constituted by slice data output from CT (Computed Tomography) apparatuses and MRI (Magnetic Resonance Imaging) apparatuses, volume data, which are output from 3DCT apparatuses and cone beam CT apparatuses, and the like are stored in the storage 4 (volume data storing means) as volume data (for example, volume data 7a obtained by imaging abdomens). In addition, volume data (for example, volume data 7b in which large intestines are extracted by analyzing the volume data 7a) obtained by analyzing the volume data are also stored in the storage 4.

The diagnosis assisting program is stored in the memory 3. The diagnosis assisting program defines: an overview image display process; a target point setting process process; a target volume setting process; a line of sight setting process; and a detailed image display process, as processes to be executed by the CPU 2. The general purpose work station functions as an overview image display means, a target point setting means, a target volume setting means, a line of sight setting means, and a detailed image display means, by the CPU 2 executing these processes according to the program.

[Embodiment 1]

First, the user interface of a diagnosis assisting apparatus according to a first embodiment will be described. The diagnosis assisting apparatus of the first embodiment provides a plurality of types of diagnosis assisting functions according to the biological tissue (organs, bones, muscles, etc.) which is a target of diagnosis. Here, an example of a user interface when a function for assisting the diagnosis of a large intestine is selected will be described.

Figure 2:
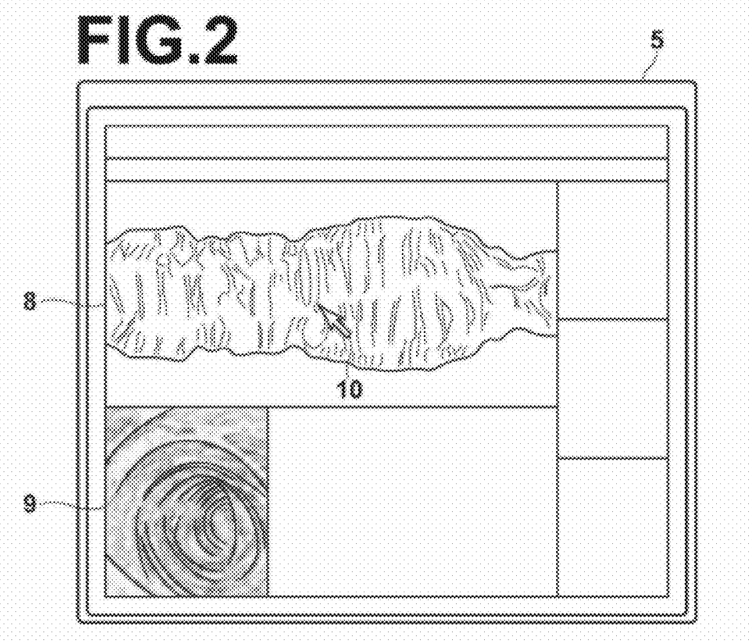
FIG. 2 is a diagram that illustrates a state in which a cursor is placed on an overview image (an extension expanded image).

When a function for assisting the diagnosis of a large intestine is selected from a menu, and an examination result (data file) which is to be the target of diagnosis is selected, an extension expanded image 8 and a virtual endoscopy image 9 are displayed on the screen of the display 5 as overview images of the large intestine, as illustrated in FIG. 2. Regions which are not displayed may be caused to sequentially appear on the screen, by dragging the extension expanded image 8 in the horizontal direction, for example. With respect to the virtual endoscopy image, the wheel of the mouse 6 may be rotated for example to move the virtual viewpoint along the core of the virtual endoscopy image toward or away from the viewer, to cause regions which are not displayed to sequentially appear on the screen. A physician can observe the entirety of the inner wall of the large intestine in a short amount of time, by performing these operations.

Figure 3:
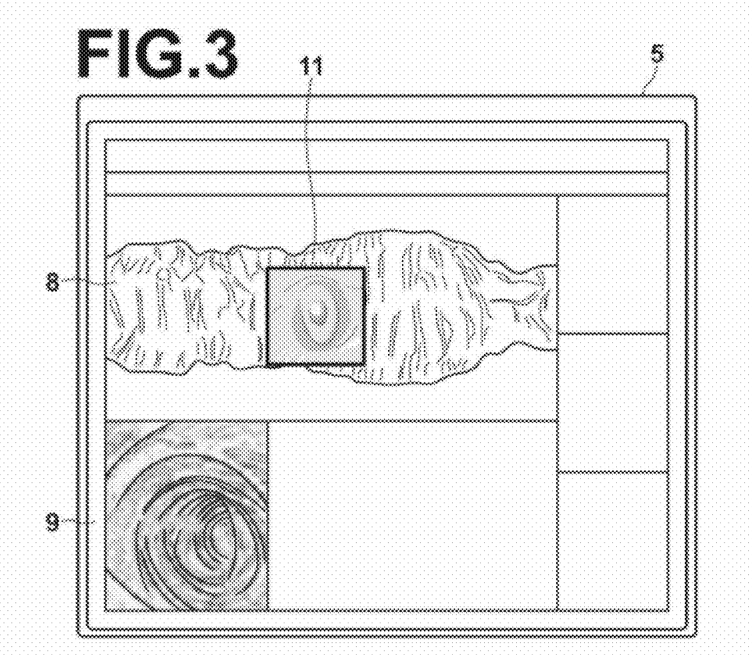
FIG. 3 is a diagram that illustrates an example of a screen in which a detailed image is displayed on an overview image (an extension expanded image).

Here, if the right button of the mouse is depressed while a cursor 10 is placed on the extension expanded image 8 as illustrated in FIG. 2, a detailed image 11 that represents the structures of the inner wall in the vicinity of the position at which the cursor 10 is placed is displayed to overlap the position of the cursor 10. The detailed image 11 which is initially displayed is an image of a section of the inner wall having the point specified by the cursor as its center, viewed from a line of sight having a direction perpendicular to the inner wall. The structures of the section of the inner wall are represented in detail and more accurately at a higher resolution in the detailed image 11 than in the overview image. The detailed image 11 disappears from the screen when the right mouse button is released.

Figure 4A:
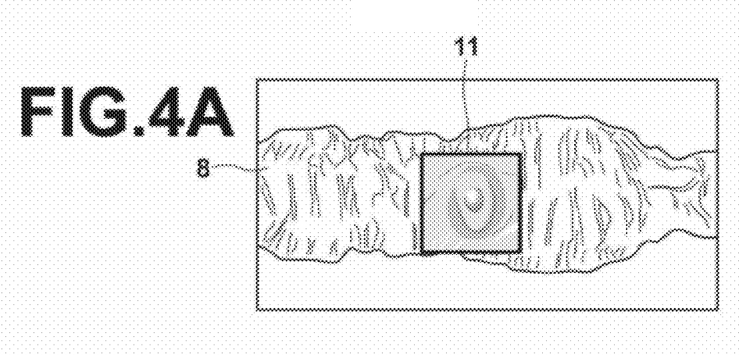
FIG. 4A is a diagram that illustrates a change in the orientation of a detailed image accompanying a change in the direction of a line of sight.
Figure 4B:
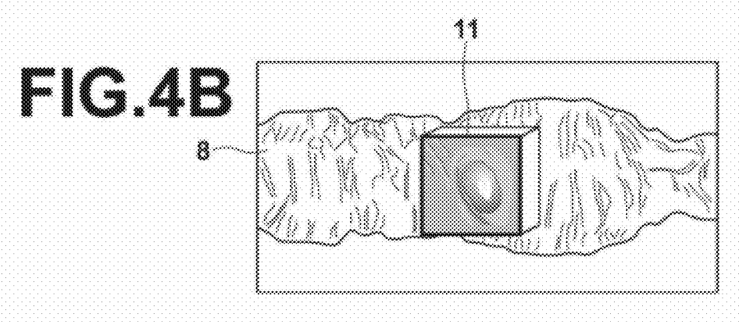
FIG. 4B is a diagram that illustrates a change in the orientation of a detailed image accompanying a change in the direction of a line of sight.
Figure 4C:
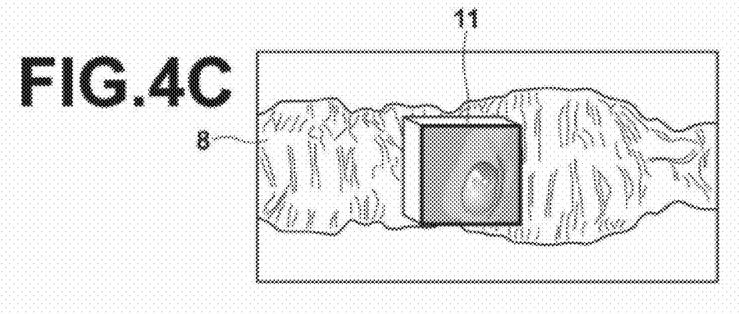
FIG. 4C is a diagram that illustrates a change in the orientation of a detailed image accompanying a change in the direction of a line of sight.
Figure 4D:
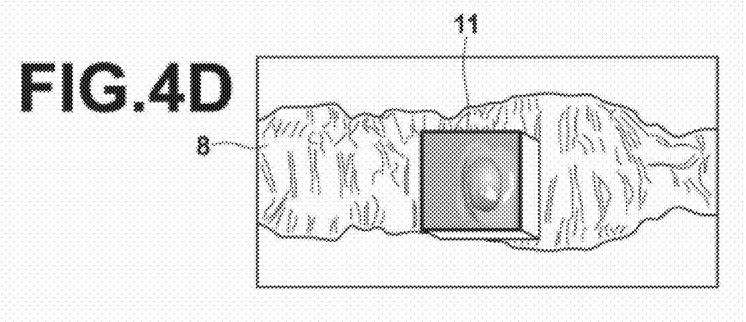
FIG. 4D is a diagram that illustrates a change in the orientation of a detailed image accompanying a change in the direction of a line of sight.

If a dragging operation is performed by the mouse in a state in which the detailed image 11 is being displayed, the orientation of the detailed image 11 on the extension expanded image 8 changes in a manner coordinated with the dragging operation. The dragging operation commands changes in the direction of the line of sight. This operation resets the line of sight when viewing the section to form an acute angle with respect to the inner wall, and an image of a view taken along the new line of sight is displayed as a detailed image. For example, FIG. 4A is a diagram that illustrates an example of an image viewed along a line of sight perpendicular to the inner wall, which is the same as FIG. 3. FIG. 4B and FIG. 4C are diagrams that illustrate examples of images taken along lines of sight inclined in the direction of the core of the large intestine (the horizontal direction in FIG. 3). FIG. 4D is a diagram that illustrates an example of an image taken along a line of sight inclined in a direction perpendicular to the core (the vertical direction in FIG. 3). The display of the detailed images is executed in a manner coordinated with the change in the direction of the line of sight. Therefore, when the dragging operation is performed, the display on the screen appears as though the detailed image 11 rotates in the depth direction.

Figure 5:
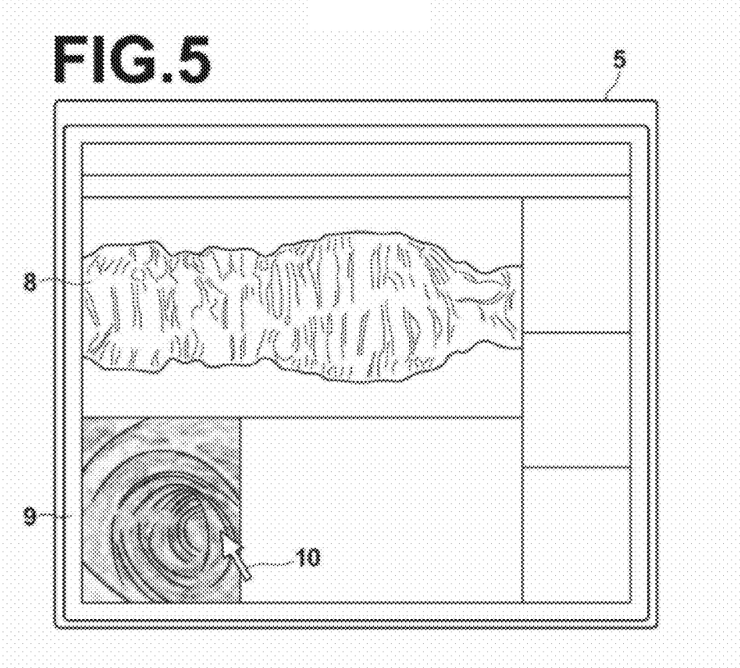
FIG. 5 is a diagram that illustrates a state in which a cursor is placed on an overview image (virtual endoscopy image).
Figure 6:
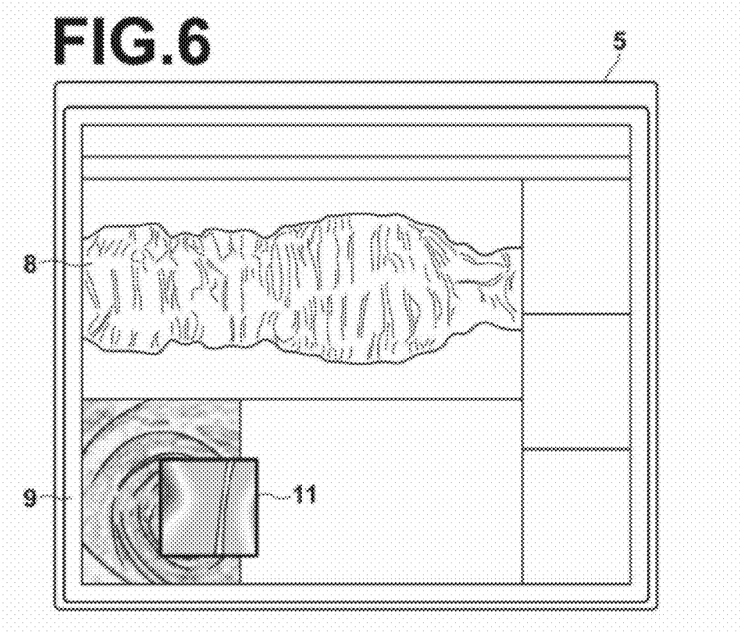
FIG. 6 is a diagram that illustrates a state in which a detailed image is displayed on an overview image (virtual endoscopy image).

Similarly, if the right mouse button is depressed in a state in which the cursor is placed on the virtual endoscopy image, a detailed image 11 that represents the structures of the inner wall in the vicinity of the position at which the cursor 10 is placed is displayed to overlap the position of the cursor 10. The detailed image 11 which is initially displayed is an image of a section of the inner wall having the point specified by the cursor as its center, viewed from a line of sight having a direction perpendicular to the inner wall. For example, FIG. 5 is a diagram that illustrates a state in which a cursor is placed on a fold within the virtual endoscopy image 9. FIG. 6 is a diagram that illustrates a state in which a detailed image 11 of the fold taken along a line of sight perpendicular to the inner wall is displayed to overlap the virtual endoscopy image 9. Alternatively, the detailed image which is initially displayed may be an image taken along a line of sight in the same direction as the line of sight of the virtual endoscopy image 9.

Figure 8:
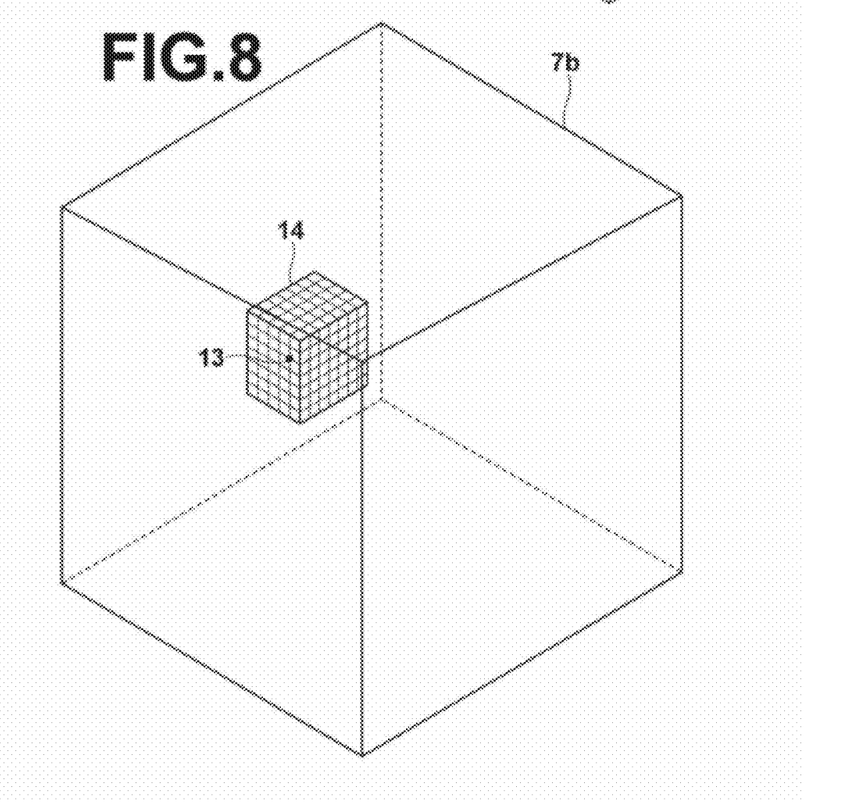
FIG. 8 is a diagram that illustrates an example of a target volume which is set within volume data.
Figure 9:
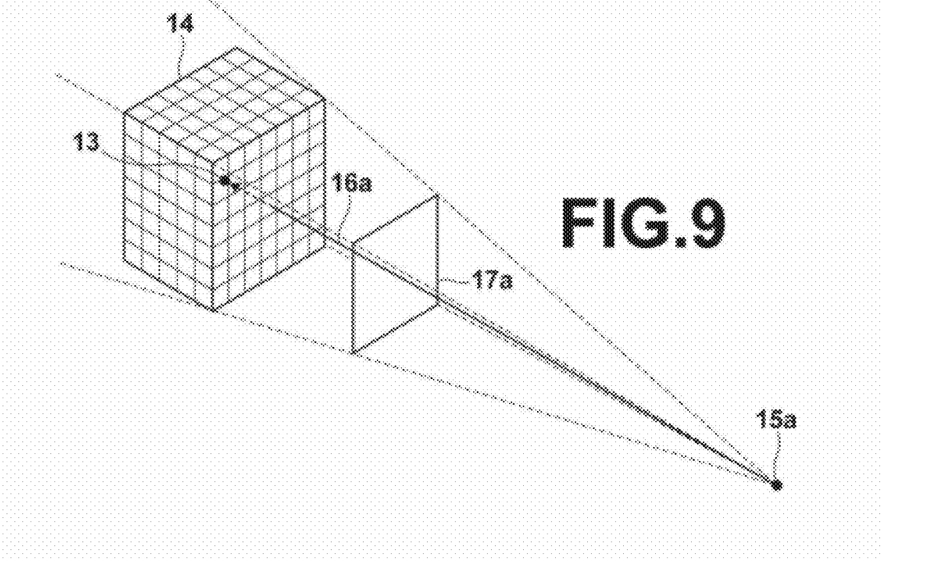
FIG. 9 is a diagram that illustrates the relationship among a target volume, a line of sight vector, and a projection plane.

According to the user interface described above, structures in the vicinity of locations where it is considered that detailed observation is necessary can be observed from a plurality of directions, by placing the cursor at such locations and performing the aforementioned operations. For example, in the case that it cannot be judged whether a structure is a polyp or a recess by viewing the extension expanded image 8 and the virtual endoscopy image 9, it may be desired to observe surfaces that do not appear in the extension expanded image 8 or the virtual endoscopy image 9, such as the rear surface of a fold. In such a case, the structure which is believed to be a polyp or structures in the vicinity of a fold of interest may be observed and confirmed in the detailed images 11. Such confirmation enables prevention of misdiagnosis such as erroneously diagnosing a recess as a polyp, overlooking diseased portions behind folds, and the like.

Next, the specific processes performed by the diagnosis assisting apparatus 1 to realize the user interface will be described. If selection of the function for assisting diagnosis of the large intestine in the menu is detected, the diagnosis assisting apparatus 1 loads volume data of an abdomen stored in the storage 4 into the memory 3.

First, the diagnosis assisting apparatus 1 executes the overview image display process. In the overview image display process, the diagnosis assisting apparatus 1 fist performs threshold value judgment on the volume data 7a, to extract regions which are estimated to be air regions. This process detects the tubular hollow organ regions (the large intestine, the small intestine, the duodenum, etc.) within the abdomen as large intestine candidate regions. Next, features of the large intestine are detected from within each candidate region, and the region from which the greatest number of such features is detected is judged to be a large intestine region. Further, the region which has been judged to be the large intestine region is displayed in a window at the upper right of the screen, and correction commands from a user are received. In the case that input of a correction command is detected, the judgment results are corrected based on the correction command. The volume data 7b illustrated in FIG. 1 is generated in this manner. Note that in the case that the volume data 7b is stored in the storage 4 in advance, the volume data 7a is loaded into the memory 3 instead of the volume data 7a, and the process for discriminating the large intestine region need not be executed.

Next, the diagnosis assisting apparatus 1 administers a thinning process onto the large intestine region, and extracts a line segment that corresponds to the core of the large intestine. Further, the spline curve interpolation is administered on the line segment to form a smooth path. Next, the diagnosis assisting apparatus 1 expands the large intestine region along the path, to generate an extension expanded image (or an extension sectional image) of the large intestine. In addition, correlative relationships among the positional coordinates of each piece of voxel data that constitutes the large intestine region and the positional coordinates of points in the extension expanded image are stored in the memory 3 during the process of generating the extension expanded image. Further, the diagnosis assisting apparatus 1 sets a viewpoint at an initial position on the path, and generates a virtual endoscopy image. Methods for generating the extension expanded image, the extension sectional image, and the virtual endoscopy image are disclosed in many documents including Patent Document 1, and therefore a detailed description thereof will be omitted. The diagnosis assisting apparatus 1 outputs the generated extension expanded image and the generated virtual endoscopy image to the display. Thereby, images such as those illustrated in FIG. 2 appear on the screen.

Figure 7:
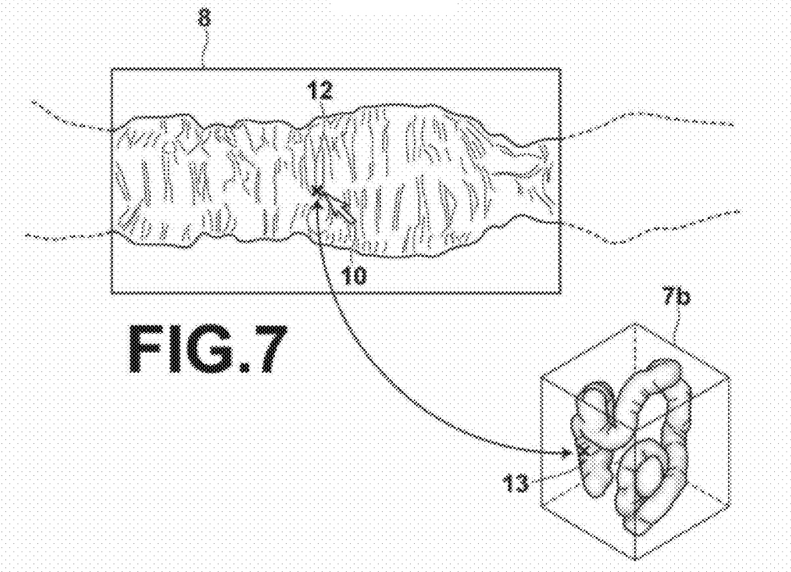
FIG. 7 is a diagram that illustrates target points within an overview image and within volume data.

Next, the target point setting process performed by the diagnosis assisting apparatus 1 will be described with reference to FIG. 7. In the target point setting process, the diagnosis assisting apparatus 1 first detects mouse operations by the user, and obtains coordinate data of a point 12 which is specified by the cursor 10. Here, the obtained coordinate data represents the positional coordinate of a point which is specified in the extension expanded image. The diagnosis assisting apparatus 1 then obtains coordinate data of a point 13 within the volume data 7b that corresponds to the specified point 12, based on the correlative relationships stored in the memory 3 when the overview image display process was executed. Then, the point on the inner wall indicated by the two pieces of obtained coordinate data is set as a target point. Note that Patent Document 1 discloses the details of a method for correlating points within an extension expanded image and points within volume data.

Next, the target volume setting process performed by the diagnosis assisting apparatus 1 will be described with reference to FIG. 8. As illustrated in FIG. 8, a target volume 14 is a section of the volume data 7b, and is constituted by a plurality of pieces of voxel data about the periphery of the point 13 which has been set as the target point.

The memory 3 has stored therein data that defines the shape and size of the target volume 14. In the first embodiment, the default definition data defines a target volume which is a parallelepiped with an upper surface having edges with lengths approximately the same as the width of a standard sized polyp, and a thickness approximately the same as the height of a standard sized polyp. The actual sizes of many polyps are those that would fit in a 10 mm×10 mm range. Therefore, the shape of the target volume 14 may be that which can represent an actual size of approximately 15 mm×15 mm. Note that the shape and the size of the target volume can be changed by rewriting the definition data. In addition, a plurality of sets of selectable definition data may be stored in the memory 3, and the target volume may be set based on the selected definition data.

The diagnosis assisting apparatus 1 determines the shape and the size of the target volume by referring to the definition data, and sets a target volume having the determined shape and size. The setting of the target volume is performed by determining the positional coordinates of pieces of voxel data that specify the shape and the size of the target volume. For example, in the case of a parallelepiped target volume, the positional coordinates of the eight corners of the parallelepiped are determined. In the case of a cylindrical target volume, the positional coordinate of the center of the upper surface of the cylinder, the radius of the cylinder (defined as the number of pieces of voxel data), and the height of the cylinder (defined as the number of pieces of voxel data) are determined. In the first embodiment, the parallelepiped target volume is set such that one of the surfaces of the target volume is parallel to the inner wall of the large intestine, and the target point 13 is positioned substantially at the center of the target volume.

Figure 10:
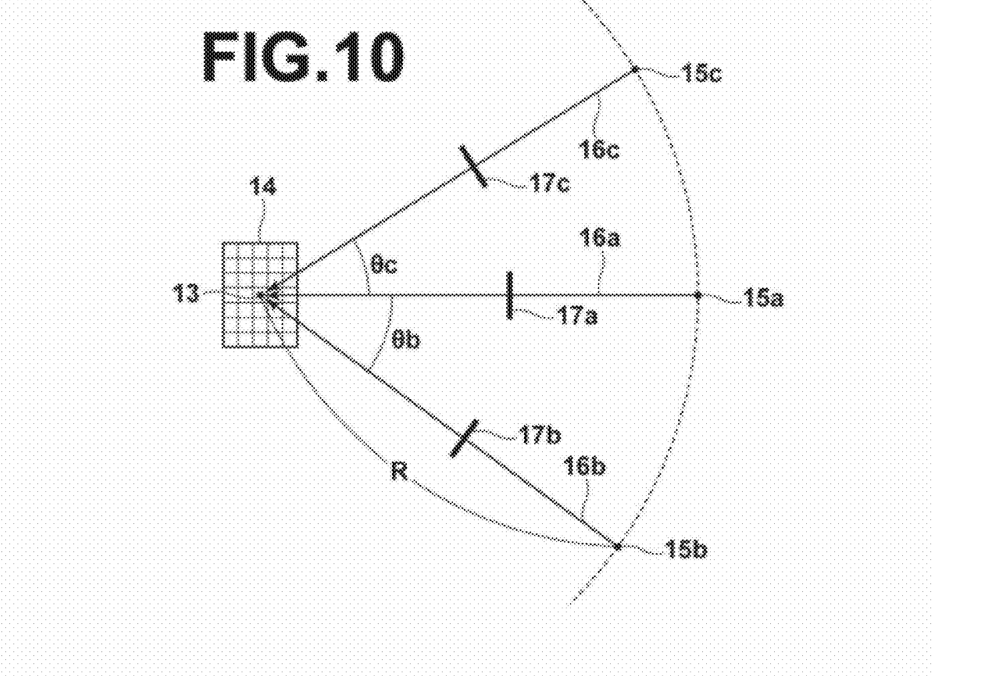
FIG. 10 is a diagram that illustrates a moving viewpoint and a changing line of sight vector.

Next, the line of sight setting process and the detailed image display process performed by the diagnosis assisting apparatus 1 will be described with reference to FIG. 9 and FIG. 10. The diagnosis assisting apparatus 1 initially sets a line of sight vector 16a having a length R having the set target point 13 as an endpoint, and a movable viewpoint 15a as a starting point. As illustrated in FIG. 9 the direction of the line of sight vector 16a which is initially set is perpendicular with respect to the inner wall of the large intestine (with respect to a surface of the target volume) The viewpoint 15a may be set along the path which was set during generation of the extension expanded image, or may be set off the path.

Next, the diagnosis assisting apparatus 1 generates a detailed image by projecting the target volume 14 onto a projection plane 17a perpendicular to the direction of the initially set line of sight vector 16a. Note that the technique employed to project the target volume 14 may be transparent projection (central projection) or parallel projection. The diagnosis assisting apparatus 1 displays the image generated by projection, that is, the detailed image, to overlap the position that the cursor is placed in the extension expanded image displayed on the screen.

When a dragging operation that commands a change in the direction of the direction of the line of sight is detected, the diagnosis assisting apparatus 1 executes the line of sight setting process and the detailed image display process again. Thereby, the starting point of the line of sight vector moves along the surface of a sphere having a radius R and the point 13 as the center and a new viewpoint 15b or 15c is set, as illustrated in FIG. 10. The directions of reset line of site vectors 16b and 16c, that is, angles θb and θc, are determined according to the amount of movement of the mouse during the dragging operation. The diagnosis assisting apparatus 1 projects the target volume 14 onto a projection plane 17b (or 17c) perpendicular to the newly set line of sight vector 16b (or 16b) each time that the direction of the line of sight vector is changed. Thereby, a detailed image is generated, which is then output to the screen. The line of sight setting process and the detailed image display process are repeatedly executed, to enable continuous display of images that represent structures in the vicinity of the target point, taken from various angles.

Note that the diagnosis assisting apparatus 1 also executes the target point setting process, the target volume setting process, the line of sight setting process, and the detailed image display process in the same manner as that described above in the case that the aforementioned mouse operations are detected in a state in which the cursor is placed on the virtual endoscopy image 9 as well.

According to the diagnosis assisting apparatus, the diagnosis assisting program, and the diagnosis assisting method of the first embodiment, physicians who perform diagnosis can visually understand the entirety of the large intestine based on the extension expanded image and the virtual endoscopy image. The physicians are enabled to freely specify points within the extension expanded image and the virtual endoscopy image that they believe require further observation. Then, detailed images that represent the structures in the vicinities of the specified points can be displayed on the screen. Therefore, efficient diagnoses become possible.

In addition, the directions of lines of sight can be set as desired during observation of the detailed images. Therefore, physicians are enabled to observe the structures in the vicinities of the specified points from various angles. Thereby, polyps and recesses, and folds and grooves which are difficult to distinguish by observation from a single direction can be correctly distinguished. Further, regions such as the rear sides of folds, which are not viewable by observation from a single direction, can be observed. At this time, the changing of the directions of the lines of sight is performed manually by the physicians. Therefore, the physicians may observe images as desired without being restricted by time.

As described previously, structures outside the range of the target volume do not appear in the detailed images. Therefore, structures in the periphery will not block lines of sight during observation. For example, if a fold is present next to a polyp to be observed, the target volume may be set to exclude the fold such that the polyp can be observed without a line of sight being blocked by the fold even if the line of sight is set from a direction in which the fold is present.

In addition, the structures (the shapes and sizes thereof) that appear in the detailed images are more accurate than those that appear in the overview images. Therefore, physicians can diagnose the sizes of polyps, etc., based on the results of observing the detailed images.

Further, the detailed images are displayed on the extension expanded image at the point where the cursor is placed. Therefore, the series of operations of specifying the target points and moving the viewpoint can be performed without moving the mouse over a great distance.

[Embodiment 2]

Next, an embodiment that utilizes a CAD detection technique as a diagnosis assisting process will be described as a second embodiment of the present invention. A diagnosis assisting apparatus of the second embodiment is the same as the apparatus of the first embodiment except for the points to be described below, and therefore, a detailed description thereof will be omitted.

Figure 11:
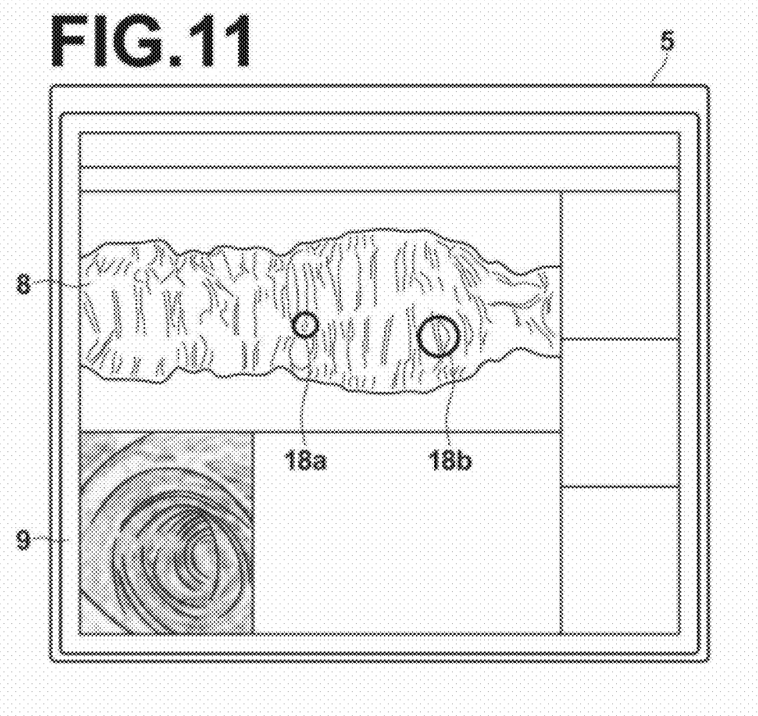
FIG. 11 is a diagram that illustrates an example of a marked overview image.

In the second embodiment, when the function for assisting diagnosis of the large intestine is selected, a screen, which is similar to that of the first embodiment, is displayed. However, an overview image and a virtual endoscopy image which have been marked at locations that require detailed observation by marks 18a and 18b are displayed on the screen, as illustrated in FIG. 11. In addition, the sizes and shapes of the detailed images which are displayed on the screen change according to the structures represented by the detailed images.

The diagnosis assisting apparatus of the second embodiment realizes this user interface by executing a characteristics detecting process on the volume data in the target point setting process. Then, diseased portions (polyps, etc.) and structures that may lead to diseased portions being overlooked (folds that form acute angles with the inner wall, etc.) are extracted based on the detected characteristics. Various methods for extracting specific structures from volume data have been proposed, including that described in paragraphs 107 and 108 of Japanese Unexamined Patent Publication No. 2007-307358. The target point setting process may use any of these known methods. When specific structures are extracted, the diagnosis assisting apparatus automatically sets the center points or the like of the extracted structures as target points, and displays marks 18a and 18b, such as circles, on the target points within the overview images.

In addition, the diagnosis assisting apparatus of the second embodiment performs a characteristics detecting process on the volume data in the vicinities of the target points in the target volume setting process. Here, features that indicate the sizes of targets for observation, such as the widths and heights of polyps and folds, are detected. Then, the shape and size of the target volume are set such that the entireties of the targets that require observation are included therein, based on the detected features.

Accordingly to the diagnosis assisting apparatus of the second embodiment, the need for users to search for locations at which detailed observation is necessary is obviated. The users may move the cursor sequentially to the marked locations, and cause the detailed images to be displayed. In addition, there is no worry that portions of polyps or folds will be omitted from the detailed images, and locations that require observation can be positively observed.

[Embodiment 3]

Next, an embodiment that generates detailed images by combining a plurality of projection techniques will be described as a third embodiment of the present invention. A diagnosis assisting apparatus of the third embodiment is the same as the apparatus of the first embodiment except for the points to be described below, and therefore, a detailed description thereof will be omitted.

Figure 12:
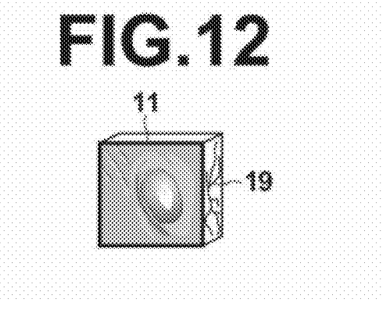
FIG. 12 is a diagram that illustrates an example of a detailed image which is generated by combining two types of projected images.

The diagnosis assisting apparatus of the third embodiment generates a transparent projection image or a parallel projection image and an HIP image of the target volume in the detailed image display process. A detailed image is generated by combining the two types of projection images. For example, the detailed image is generated by fusing the entireties of the two types of projection images. Alternatively, a detailed image, in which a portion is a transparent projection image and another portion is an MIP image, may be generated. FIG. 12 is a diagram that illustrates an example of a detailed image 11 which is generated by combining a transparent projection image that represents the structures of an inner wall and an NIP image that represents blood vessels 19. At this time, an MPVR (Multi Projection Volume Reconstruction) image may be combined with the transparent projection image instead of the NIP image.

Whether a polyp at the inner wall of the large intestine is malignant or benign is commonly judged by observing the states of blood vessels in the periphery of the polyp. Although blood vessels do not appear in transparent projection images, they do appear in MIP images. Therefore, information which is effective in assisting judgment regarding whether a polyp is malignant or benign can be provided by displaying the detailed image generated by combining the transparent projection image and the MIP image.

[Embodiment 4]

Next, an embodiment that displays overview images and detailed images for different imaging body positions will be described as a fourth embodiment of the present invention. A diagnosis assisting apparatus of the fourth embodiment is the same as the apparatus of the first embodiment except for the points to be described below, and therefore, a detailed description thereof will be omitted.

During examinations of the large intestine, there are cases in which a plurality of imaging operations are performed with different imaging body positions, in order to move residue that may obstruct observation. That is, there are cases in which a plurality of sets of volume data for different body positions are obtained by imaging. Commonly, imaging is performed with a patient in the supine and prone positions, to obtain two sets of volume data. Note that there are cases in which imaging is further performed with the patient in lateral recumbent positions, to obtain three or more sets of volume data.

Figure 13:
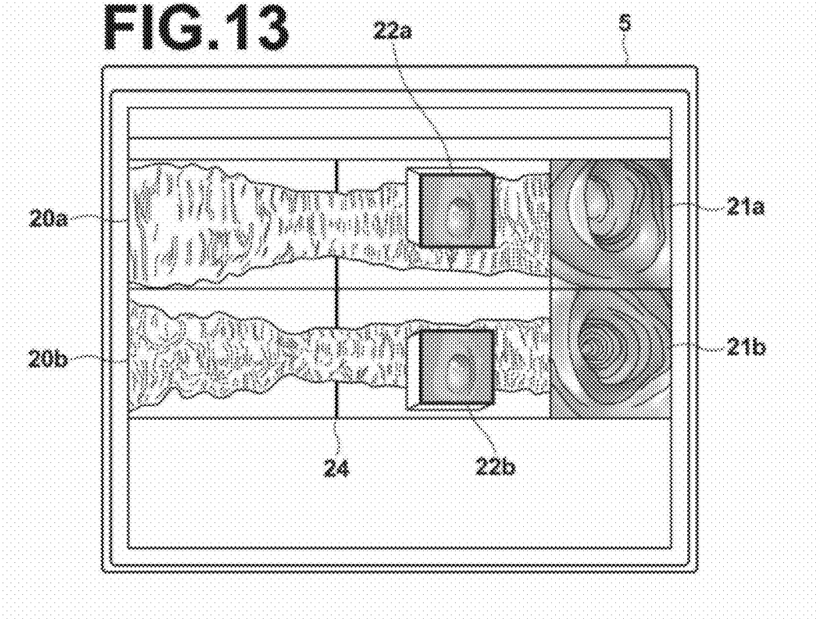
FIG. 13 is a diagram that illustrates an example of a screen in which overview images for different body positions are displayed.

In the case that volume data for a plurality of body positions are stored, the diagnosis assisting apparatus of the fourth embodiment displays overview images for each body position, as illustrated in FIG. 13. FIG. 13 illustrates a screen in which four types of overview images, which are: an extension expanded image 20a generated from volume data Vs obtained by imaging in the supine position; a virtual endoscopy image 21a generated from the volume data Vs obtained by imaging in the supine position; an extension expanded image 20b generated from volume data Vp obtained by imaging in the prone position; and a virtual endoscopy image 21b generated from the volume data Vp obtained by imaging in the prone position, are displayed. A viewpoint setting line 24 which is movable by cursor operations is displayed on the extension expanded images 20a and 20b. The virtual endoscopy images 21a and 21b are images having positions along the path of the large intestine specified by the viewpoint setting line 24 as viewpoints.

When a user performs an operation to specify a target point within an overview image of a certain imaging body position, the diagnosis assisting apparatus sets a target point and a target volume within the set of volume data employed to generate the overview image. Then, the diagnosis assisting apparatus displays a detailed image generated by projecting the target volume. For example, in the case that a target point is set within the supine extension expanded image 20a, a target point and a target volume are set within the volume data Vs obtained by imaging in the supine position, then a detailed image 22a is generated and displayed. This process is the same as the process performed by the diagnosis assisting apparatus of the first embodiment. However, the diagnosis assisting apparatus of the fourth embodiment additionally generates and displays a detailed image 22b for the overview image (the extension expanded image 20b of the prone position) in which a target point was not specified.

Figure 14:
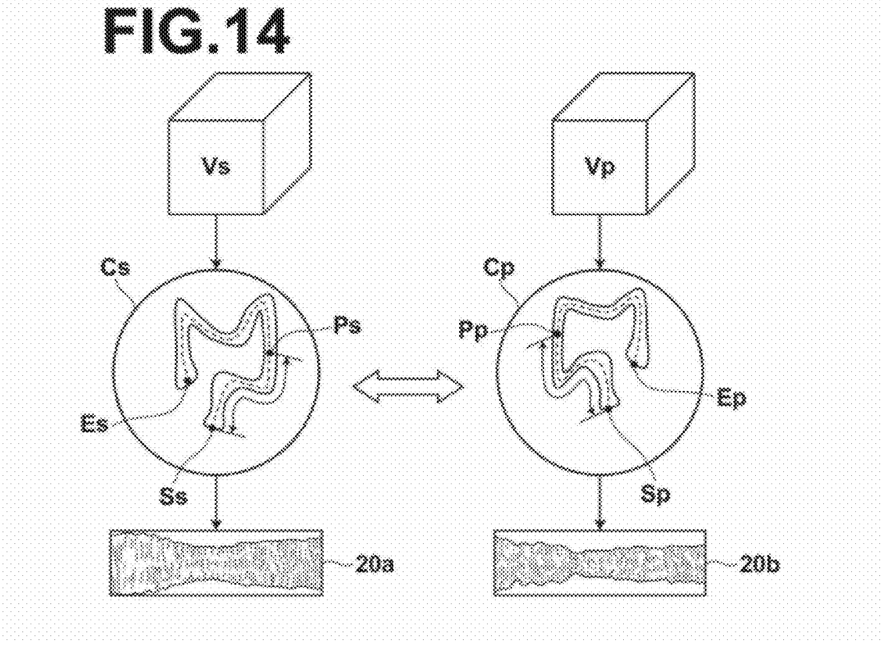
FIG. 14 is a diagram for explaining a method for generating detailed images for different body positions.

The diagnosis assisting apparatus of the fourth embodiment performs a correlating process as illustrated in FIG. 14 during the overview image generating process, that is, when the extension expanded images 20a and 20b are generated, in order to generate and display the detailed image 22b. As illustrated in FIG. 14, the diagnosis assisting apparatus extracts large intestine regions Cs and Cp from the volume data Vs obtained by imaging in the supine position and the volume data Vp obtained by imaging in the prone position, respectively. Then, paths of the large intestine (denoted by the dotted line) are determined by a thinning process. At this time, the positional coordinates of a starting point Ss of the path extracted from the volume data Vs and the positional coordinates of a starting point Sp of the path extracted from the volume data Vp are stored in the memory 3. Alternatively, the positional coordinates of endpoints Es and Ep may be stored instead of the positional coordinates of the starting points.

Further, distances from the starting points (or the endpoints) are measured at points along the paths, and points at the same distances from the starting points are stored as points that correspond to each other. Because the shape of the large intestine differs between the supine position and the prone position, the large intestine region Cs and the large intestine region Cp will not necessarily be of the same shape, as illustrated in FIG. 14. However, if the distance from the starting point Ss to a point Ps measured along the path and the distance from the starting point Sp to a point Pp measured along the path are equal, it can be confirmed that the point Ps and the point Pp represent the same anatomical point.

The diagnosis assisting apparatus specifies a point along the path closest to the target point within the volume data Vs after the target point is set within the volume data Vs in the target point setting process. Then, the diagnosis assisting apparatus refers to the correlative relationships stored in the memory 3, and specifies a point within the volume data Vp that corresponds to the point along the path within the volume data Vs. Further, an initially set direction of a line of sight vector is obtained, and the intersection between the line of sight vector and the inner wall is set as the target point within the volume data Vp. Thereby, a target volume necessary to generate the detailed image 22b can be set within the volume data Vp.

In addition, correlative relationships among the positional coordinates of each piece of voxel data that constitutes the large intestine region Cp and the positional coordinates of each piece of voxel data that constitutes the large intestine region Cs are stored in the memory 3 during the step of generating the extension expanded image, in the same manner as in the first embodiment. Accordingly, the positional coordinate of a corresponding point in the extension expanded image 20b, that is, the display position of the detailed image 22b, is determined from the positional coordinate of the target point within the volume data Vp. Thereby, the screen illustrated in FIG. 13 can be displayed.

Note that in the method described above, the positional coordinate of the target point in the extension expanded image 20b is determined after the target point is specified within the volume data Vp. Alternatively, the setting of the target points can be performed in reverse order. For example, if non rigid positional alignment is performed between the extension expanded images 20a and 20b in advance, the point within the extension expanded image 20b that corresponds to the target point can be immediately specified from the positional coordinate of the target point within the extension expanded image 20a. In this case, the target point within the volume data Vp may be specified based on the target point specified in the extension expanded image 20b, by utilizing the correlative relationships stored in the memory.

If the correlative relationships stored in the memory 3 are utilized, the direction of the line of sight of a detailed image can be changed in a coordinated mariner with a change in direction of the line of sight of another detailed image when a command to change the direction of the line of sight within the other detailed image is input. Alternatively, the directions of the lines of sight may be changed individually within the detailed images 22a and 22b.

In addition, FIG. 13 illustrates a case in which the target point is set at a position remote from the viewpoint setting line 24. In the case that the target point is set on the viewpoint setting line 24, detailed images are displayed to overlap the virtual endoscopy images 21a and 21b, in addition to the detailed images displayed to overlap the extension expanded images 20a and 20b. *Alternatively, detailed images may be displayed to overlap the virtual endoscopy images in the case that the target point is set on the viewpoint setting line* 24, *and detailed images may be displayed to overlap the extension expanded images in the case that the target point is set remote from the viewpoint setting line* 24.

According to the diagnosis assisting apparatus of the fourth embodiment, the same location can be observed within images obtained by imaging with different body positions, even in cases that residue may obstruct observation. That is, locations that require observation can be positively observed, and diagnostic accuracy can be improved.

[Other Embodiments]

Four embodiments have been described above. Other embodiments that combine the processes described with respect to the above embodiments may also be considered.

For example, with respect to the setting of the target points, the target point setting process of the first embodiment (manual setting) and the target point setting process of the second embodiment (automatic setting) may be selectable via a menu.

In addition, the target points may be performed manually, not by the characteristics detecting process, and the target volume may be set based on the results of feature detection. Conversely, the target points may be set automatically based on the results of feature detection, and the target volume may be set based on the definition data stored in the memory.

In addition, with respect to the detailed image display process, the plurality of types of detailed images as described in the first through fourth embodiments may be generated, and display of the detailed images may be switched by menu selection or the like.

In the line of sight setting processes of the first through fourth embodiments, the viewpoint is moved in response to operations of the mouse. Alternatively, the viewpoint maybe moved automatically along the aforementioned sphere, and fixed when a mouse operation is performed.

In the detailed image display processes of the first through fourth embodiments, the detailed images are displayed to overlap the overview images. Alternatively, the detailed images may be displayed in a window separate from that in which the overview images are displayed.

In the detailed image display processes of the first through fourth embodiments, a single detailed image is displayed for each overview image. Alternatively, a plurality of detailed images may be generated for each of a plurality of target points, and the plurality of detailed images may be displayed alongside each other on the screen. Further, the diagnosis assisting apparatus may be provided with a function of printing the detailed images which are displayed alongside each other at once.

Further, volume data of the same subject obtained in temporal series may be loaded, a target point may be set at the same position, and detailed images generated from past volume data and a detailed image generated from the newest volume data may be displayed alongside each other. In this embodiment, it is desirable for the directions of lines of sight to be changed for all of the detailed images in a coordinated manner in the case that a command to change the direction of the line of sight is input with respect to one of the detailed images.

In the descriptions of the first through fourth embodiments, a mouse was described as an example of the input device. However, it goes without saying that other input devices may be employed.

For example, joysticks and the like are suited for operations for rotating detailed images. As a further alternative, a touch panel may be employed instead of the display 5, and operations may be input via the touch panel.

The processes which are executed by a single diagnosis assisting apparatus in the first through fourth embodiments may be divided among a plurality of computers, and executed thereby.

As described above, the present invention is not limited to the embodiments described above. Various modifications are possible as long as they do not stray from the spirit of the present invention. In addition, the present invention is not limited to assisting diagnosis of the large intestine, but may be employed to assist diagnosis of various biological tissues, such as other organs, blood vessels, bones, and muscles. Further, the present invention is not limited to assisting diagnosis of biological organisms, but may also be applied to baggage inspections at airports, for example.

The invention claimed is:

1. A diagnosis assisting apparatus, characterized by comprising:

volume data storing unit, for storing volume data constituted by data obtained by imaging a subject;

overview image display unit, for generating overview images of structures that constitute the subject based on the volume data, and for displaying the overview images on a screen;

target point setting unit, for setting at least one point within the overview images and at least one point within the volume data corresponding to the at least one point within the overview images as set target points;

target volume setting unit, for setting a target volume that includes the set target points within the volume data;

line of sight setting unit, for setting line of sight vectors within the volume data having the set target points as endpoints and a movable viewpoint as a starting point, and for changing the directions of the line of sight vectors by moving the viewpoints, while maintaining the set target point as the endpoint of the line of sight vectors; and detailed image display unit, for projecting the set target volume onto projection planes perpendicular to the directions of the set line of sight vectors to generate detailed images that represent details of the structure in the vicinity of the set target points, and for displaying the detailed images on the screen, wherein the structures outside the ran of the set target volume do not appear in the generated detailed images.

2. A diagnosis assisting apparatus as defined in claim 1, wherein:

the overview image display unit displays one of an extension expanded image and an extension sectional image as one of the overview images in the case that the structure is a tubular structure.

3. A diagnosis assisting apparatus as defined in claim 1, wherein:

the target point setting unit detects user operations that specify points within the overview images displayed on the screen, and sets the point specified by the user operations and the points within the volume data corresponding to the points as the set target points.

4. A diagnosis assisting apparatus as defined in claim 1, wherein:

the target point setting unit detects characteristic portions of the structure by analyzing the volume data, and sets points within the overview images that indicate the positions of the characteristic portions and points within the volume data that indicate the positions of the characteristic portions as the set target points.

5. A diagnosis assisting apparatus as defined in claim 1, wherein:

the target volume setting unit refers to data regarding the shape and the size of a target volume which is stored in a predetermined recording medium, and sets a target volume having a shape and a size indicated by the data.

6. A diagnosis assisting apparatus as defined in claim 1, wherein:

the target volume setting unit detects characteristic portions of the structure by analyzing the volume data, and sets a target volume having a shape and a size which are determined based on the shapes and the sizes of the characteristic portions.

7. A diagnosis assisting apparatus as defined in claim 1, wherein:
the line of sight setting unit detects user operations that command movement of the viewpoint, and moves the viewpoint based on the user operations.

8. A diagnosis assisting apparatus as defined in claim 1, wherein:
the detailed image display unit displays the detailed images overlapped with each other at the positions of the overview images at which the set target points are set.

9. A diagnosis assisting apparatus as defined in claim 1, wherein:
the detailed image display unit generates a plurality of projected images of the set target volume by a plurality of projection methods, and combines the plurality of projected images to generate the detailed images.

10. A diagnosis assisting apparatus as defined in claim 1, wherein:
the overview image display unit generates and displays a plurality of overview images for each of a plurality of body positions, based on sets of volume data related to a plurality of body positions obtained by performing imaging with different body positions; and
the detailed image display unit generates and displays a plurality of detailed images employing target volumes which are set in each of the plurality of sets of volume data for each of the plurality of body positions.

11. A non-transitory computer readable medium having a diagnosis assisting program recorded therein, characterized by the diagnosis assisting program causing at least one computer to execute:
a volume data storing step, for storing volume data constituted by data obtained by imaging a subject;
an overview image display step, for generating overview images of structures that constitute the subject based on the volume data, and for displaying the overview images on a screen;
a target point setting step, for setting at least one point within the overview images and at least one point within the volume data corresponding to the at least one point within the overview images as set target points;
a target volume setting step, for setting a target volume that includes the set target points within the volume data;
a line of sight setting step, for setting line of sight vectors within the volume data having the set target points as endpoints and a movable viewpoint as a starting point, and for changing the directions of the line of sight vectors by moving the viewpoints, while maintaining the set target point as the endpoint of the line of sight vectors; and
a detailed image display step, for projecting the set target volume onto projection planes perpendicular to the directions of the set line of sight vectors to generate detailed images that represent details of the structure in the vicinity of the set target points, and for displaying the detailed images on the screen,
wherein e structure outside the range of the set target volume do not appear in the generated detailed images.

12. A diagnosis assisting method, characterized by causing at least one computer to execute:
a volume data storing step, for storing volume data constituted by data obtained by imaging a subject;
an overview image display step, for generating overview images of structures that constitute the subject based on the volume data, and for displaying the overview images on a screen;
a target point setting step, for setting at least one point within the overview images and at least one point within the volume data corresponding to the at least one point within the overview images as set target points;
a target volume setting step, for setting a target volume that includes the set target points within the volume data;
a line of sight setting step, for setting line of sight vectors within the volume data having the set target points as endpoints and a movable viewpoint as a starting point, and for changing the directions of the line of sight vectors by moving the viewpoints, while maintaining the set target point as the endpoint of the line of sight vectors; and
a detailed image display step, for projecting the set target volume onto projection planes perpendicular to the directions of the set line of sight vectors to generate detailed images that represent details of the structure in the vicinity of the set target points, and for displaying the detailed images on the screen,
wherein the structures outside the range of the set target volume do not appear in the generated detailed images.

13. The diagnosis assisting apparatus of claim 1, wherein the target volume setting unit sets the target volume to exclude an obstruction so as to generate the detailed images without the line of sight being blocked by the obstruction.

14. The non-transitory computer readable medium of claim 11, wherein the target volume setting step comprises setting the target volume to exclude an obstruction so as to generate the detailed images without the line of sight being blocked by the obstruction.

15. The diagnosis assisting method of claim 12, wherein the target volume setting step comprises setting the target volume to exclude an obstruction so as to generate the detailed images without the line of sight being blocked by the obstruction.

* * * * *